United States Patent
Goldenberg

(10) Patent No.: US 7,201,890 B2
(45) Date of Patent: *Apr. 10, 2007

(54) INTRAOPERATIVE, INTRAVASCULAR AND ENDOSCOPIC TUMOR AND LESION DETECTION, BIOPSY AND THERAPY

(75) Inventor: Milton D. Goldenberg, Mendham, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 675 days.

This patent is subject to a terminal disclaimer.

(21) Appl. No.: 10/086,637

(22) Filed: Mar. 4, 2002

(65) Prior Publication Data

US 2002/0146369 A1 Oct. 10, 2002

Related U.S. Application Data

(60) Division of application No. 09/348,818, filed on Jul. 8, 1999, now Pat. No. 6,387,350, which is a division of application No. 09/021,392, filed on Feb. 10, 1998, now Pat. No. 6,096,289, which is a continuation-in-part of application No. 08/293,313, filed on Aug. 22, 1994, now Pat. No. 5,716,595, which is a continuation of application No. 07/879,857, filed on May 6, 1992, now abandoned.

(51) Int. Cl.
*A61K 51/00* (2006.01)
*A61K 39/00* (2006.01)

(52) U.S. Cl. .................. 424/1.49; 424/1.57; 424/1.69; 424/178.1

(58) Field of Classification Search ............... 424/1.57, 424/1.49, 1.69, 178.1, 181.1; 530/391.3, 530/391.5
See application file for complete search history.

(56) References Cited

U.S. PATENT DOCUMENTS

| | | | |
|---|---|---|---|
| 4,331,647 A | 5/1982 | Goldenberg | |
| 4,348,376 A | 9/1982 | Goldenberg | |
| 4,361,544 A | 11/1982 | Goldenberg | |
| 4,444,744 A | 4/1984 | Goldenberg | |
| 4,460,561 A | 7/1984 | Goldenberg | |
| 4,474,893 A | 10/1984 | Reading | |
| 4,624,846 A | 11/1986 | Goldenberg | |
| 4,706,652 A * | 11/1987 | Horowitz | 600/7 |
| 4,782,840 A | 11/1988 | Martin, Jr. et al. | |
| 4,818,709 A | 4/1989 | Primus et al. | |
| 4,859,449 A | 8/1989 | Mattes | |
| 4,932,412 A | 6/1990 | Goldenberg | |
| 4,946,778 A | 8/1990 | Ladner et al. | |
| 5,057,313 A | 10/1991 | Shih et al. | |
| 5,256,395 A | 10/1993 | Barbet et al. | |
| 5,274,076 A | 12/1993 | Barbet et al. | |

OTHER PUBLICATIONS

Aitken et al., "A Gamma-Detecting Probe for Radioimmune Detection of CEA- Producing Tumors," *Diseases of the Colon & Rectum* vol. 27, No. 5, (1984), pp. 279-282, American Society.

Allen et al., "Combined Laser Therapy and Endobronchial Radiotherapy for Unresectable Lung Carcinoma With Bronchial Obstruction," *American Journal of Surgery* vol. 150, (1985), pp. 71-77.

Better et al., "*Escherichia coli* Secretion of an Active Chimeric Antibody Fragment," *Science* vol. 240, (1988), pp. 1041-1042.

Carter et al., "High Level *Escherichia coli* Expression and Production of a Bivalent Humanized Antibody Fragment," *Biotechnology* vol. 10, (1992), pp. 163-167.

Fleischer, "Endoscopic Laser Therapy for Gastrointestinal Disease," *Acrh. Intern. Med.* vol. 144, No. 6, (1984), pp. 1225-1230.

Hirano et al., "Photodynamic Cancer Diagnosis and Treatment System Consisting of Pulse Lasers and Endoscopic Spectro-Image Analyzer," *Lasers in the Life Sciences* vol. 3, No. 2, (1989), pp. 89-116.

Hunter et al., "Lasers in Endoscopic Gastrointestinal Surgery," *The American Journal of Surgery*, vol. 148, (1984), pp. 736-741.

Krishnan et al., "Chimerization of Mu-9: A Colon-Specific Antigen-p Antibody Reactive with Gastrointestinal Carcinomas," *Cancer*, vol. 80, No. 12, (1987), pp. 2667-2674.

Leung et al., "Bacterial Expression of Kemptide Fusion Protein Facilities $^{32}P$ labeling of a Humanized, Anti- Carcinoembryonic Antigen (hMN-14) Antibody Fragment," *Cancer Research*, vol. 55, No. 23, (1995), pp. 5968-5972.

Milstein et al., "Hybrid Hybridomas and the Production of Bi-Specific Monoclonal Antibodies," *Immunology Today*, vol. 5 No. 10, (1984), pp. 299-304.

Paganelli et al., "Three-Stop Monoclonal Antibody Tumor Targeting in Carcinoembyronic Antigen Positive Patients," *Cancer Research*, vol. 51, No. 21, (1991), pp. 5960-5966.

Profio et al., "Flourescence Diagnosis of Cancer,", *Advances in Experimental Medicine and Biology*, vol. 193, pp. 43-50, 1985.

Schray et al., "Management of Malignant Airway Obstruction: Clinical and Dosimetric Considerations Using An Iridium-192 Afterloading Technique in Conjunction with the Neodymium-Yag Laser," *Int. J. Radiation Oncology Biol. Phys.*, vol. 11, No. 2, (1985), pp. 403-409.

(Continued)

*Primary Examiner*—Michael G. Hartley
(74) *Attorney, Agent, or Firm*—Faegre & Benson LLP

(57) ABSTRACT

Methods are provided for close-range intraoperative, endoscopic and intravascular detection and treatment of lesions, including tumors and non-malignant lesions. The methods use antibody fragments or subfragments labeled with isotopic and non-isotopic agents. Also provided are methods for detection and treatment of lesions with photodynamic agents and methods of treating lesions with a protein conjugated to an agent capable of being activated to emit Auger electron or other ionizing radiation. Compositions and kits useful in the above methods are also provided.

15 Claims, 2 Drawing Sheets

OTHER PUBLICATIONS

Scerra et al., "Assembly of a Functional Immunoglobulin $F_v$ Fragment in *Escherichia coli,*" *Science*, vol. 240, (1988), pp. 1038-1041.

Studier et al., "Use of Bacteriophage T7 RNA Polymerase to Direct Selective High-Level Expression of Cloned Genes," *J. Mol. Biol.*, vol. 189, No. 1, (1986), pp. 113-130.

Tatsuta et al., "Diagnosis of Gastric Cancers With Flourescein-Labeled Monoclonal Antibodies to Carcinoembryonic Antigen," *Lasers in Surgery and Medicine*, vol. 9, No. 4, (1989).

Wood et al., "Tumor Ablation by Endoscopic Nd: YAG Laser," *The American Journal of Gastroenterology*, vol. 80, No. 9 (1985), pp. 715-718.

Profio, "Review of Flourescence Diagnosis Using Porphyrins," SPIE—The International Society For Optical Engineering, vol. 907, (1988), pp. 150-156.

Paganelli et al., "Monoclonal Antibody Pretargeting Techniques for Tumour Localization: The Avidin-Biotin System," *Nuclear Medicine Communications*, vol. 12, (1991), pp. 211-234.

Pelegrin et al., "Antibody-Flourescein Conjugates for Photoimmunodiagnosis of Human Colon Carcinoma in Nude Mice," *Cancer*, vol. 67, (1991), pp. 2529-2537.

Van Den Bergh, "Lighy and Porphyrins in Cancer Therapy," *Chem.*, Britain, vol. 22, (1986), pp. 430-439.

Dougherty et al., "Photoradiation Therapy for the Treatment of Malignant Tumors," *Cancer Research*, vol. 38, (1978), pp. 2628-2635.

Dougherty et al., "Photosensitizers: Therapy and Detection of Malignant Tumors," *Photochem and Photobiology*, vol. 45, No. 6, (1987), pp. 879-889.

Doiron et al., "Flourescence Bronchoscopy for Detection of Lung Cancer," *Chest*, vol. 76, No. 1, (1979), pp. 27-32.

Mew et al., "Photoimmunotherapy: Treatment of Animal Tumors with Tumor-Specific Monocional Antibody-Hematoporphyrin Conjugates," *Journal of Immunology*, vol. 130, No. 3, (1983), pp. 1473-1477.

Mew et al., "Ability of Specific Monoclonal Antibodies and Conventional Antisera Conjugated to Hematoporphyrin to Label and Kill Selected Cell Lines Subsequent to Light Activation," *Cancer Research*, vol. 45, (1985), pp. 4380-4386.

Oseroff et al., "Antibody- Targeted Photolysis: Selective Photodestruction of Human T-Cell Leukemia Cells Using Monoclonal Antibody-Chlorin $\theta_6$ Conjugates," *Proc. Natl. Acad. Sci. USA*, vol. 83, (1986), pp. 8744-8748.

Oseroff et al., "Strategies for Selective Cancer Photochemotherapy: Antibody- Targeted and Selective Carcinoma Cell Photolysis," *Photochemistry and Photobiology*, vol. 46, No. 1, (1987), pp. 83-96.

Hasan et al., "Laser-Induced Selective Cytotoxicity Using Monoclonal Antibody-Chromophore Conjugates," *Immunity to Cancer*, vol. II, (1989), pp. 471-477.

Adams et al., "Highly Specific *in Vivo* Tumor Targeting by Monovalent and Divalent Forms of 741F8 Anti-c-*erb*B-2 Single-Chain $F_v$," *Cancer Research*, vol. 53, (1993), pp. 4026-4034.

Haunschild et al., "Pharmacokinetic Properties of Bivalant Miniantibodies and Comparison to Other Immunoglobulin Forms," *Antibody, Immunoconjugates and Radiopharmaceuticals*, vol. 8, No. 2, (1995), pp. 111-128.

Tai et al., "Targeting c-erB-2 Expressing Tumors Using Single-Chain FV Monomers and Dimers," *Cancer Research*, vol. 55, (1995), pp. 5983-5989.

\* cited by examiner

INTRAOPERATIVE, INTRAVASCULAR AND ENDOSCOPIC TUMOR AND LESION DETECTION, BIOPSY AND THERAPY

This application is a continuation-in-part of U.S. Ser. No. 08/293,313, filed on Aug. 22, 1994, now U.S. Pat. No. 5,716,595, which is a continuation of U.S. Ser. No. 07/879,857, filed on May 6, 1992, now abandoned. These cited applications are incorporated herein in their entirety by reference.

BACKGROUND OF THE INVENTION

1. Field of the Invention

The present invention relates to improved methods for detecting and treating tumors and lesions and obtaining biopsy material in the course of intraoperative, laparoscopic, intravascular, and endoscopic examination using a small detection instrument or monitor. In preferred embodiments, the methods utilize a labeled divalent single chain antibody fragment or subfragment with a molecular weight of 85,000 daltons or less that specifically binds to an antigen produced by or associated with the tumors or lesions. Alternatively, bispecific F(ab)$_2$ and F(ab')$_2$ fragments can also be used for pre-targeting according to the present invention, if non-targeted fragments are cleared, and a bivalent diagnostic hapten is then administered to facilitate target detection and possibly other procedures within 48 hours of the first injection.

2. Description of the Prior Art

Surgical resection remains the primary curative approach in the management of cancer. Radioimmunodetection (RAID) is used to locate and stage tumors, and to monitor post-operative patients, by external imaging, after injection of a radiolabeled antibody. Antibodies and/or antibody fragments which specifically bind antigens produced by or associated with tumors ("anti-cancer antibodies") are used as carriers for radiolabels in RAID. It will be appreciated, that a tumor antigen can serve as a target for an antibody carrier even if it is not present in serum in a detectable amount.

Resolution is affected by several factors that can limit the size of a tumor, especially a metastasis, which can be imaged by RAID. Non-invasive RAID is inherently limited by the distance between the radiation detector and the tumor. In the case of small, deep-seated metastatic tumors, this becomes the limiting factor in their detection.

Second-look surgery has been practiced where recurrence of a previously excised primary tumor was indicated by elevated levels of tumor marker, e.g., carcinoembryonic antigen (CEA). Recently, a small gamma detection probe has been developed which is capable of detecting gamma emission at short distances. Its intraoperative use in second-look surgery has been reported to provide important information to the surgeon for determining safe margins for resection and for detecting small metastases, by Aitken et al., *Dis. Colon Rectum*, 27, 279–282(1984).

Nevertheless, elevated background radiation levels can interfere with and vitiate the advantage of short measuring distances in this technique. In addition, non-specific immunoglobulin uptake by tumor tissue can complicate diagnosis.

U.S. Pat. No. 4,782,840 discloses a method for reducing the effect of elevated background radiation levels during surgery. The method is to inject the patient with antibodies specific for neoplastic tissue and which are labeled with radioisotopes having a suitably long half-life, such as Iodine-125. After injection of the radiolabled antibody, the surgery is delayed at least 7–10 days, preferably 14–21 days, to allow any unbound radiolabeled antibody to be cleared to a low bloodpool, background level.

U.S. Pat. No. 4,932,412 discloses methods for reducing or correcting for non-specific background radiation during intraoperative detection. The methods include the administration to a patient who has received a radiolabeled primary antibody, of a contrast agent, subtraction agent or second antibody which binds the primary antibody.

Tumors can be detected in body cavities by means of directly or indirectly viewing various structures to which light is delivered and then collected. Lesions at any body site can be viewed so long as nonionizing radiation can be delivered and recaptured from these structures.

The prior art discloses improvements of such imaging approaches by using certain dyes that are accreted by lesions, such as tumors, which are in turn activated by a specific frequency of light. These improvements are described in Dougherty et al., *Cancer Res.* 38:2628, 1978; Dougherty, T. J., *Photochem. Photobiol.* 45:879, 1987; Jori and Perria, eds., *Photodynamic Therapy of Tumors and Other Diseases*; Padua: Libreria Progetto, 1985; Profio, *Proc. Soc. Photoopt. Instr. Eng.* 907:150, 1988; Doiron and Gomer, eds., *Porphyrin Localization and Treatment of Tumors*; New York: Alan Liss, 1984; Hayata and Dougherty, *Lasers and Hematoporphyrin Derivative in Cancer*; Tokyo: Igaku-Shoin, 1984; and van den Bergh, *Chem. Britain* 22:430, 1986, incorporated herein in their entirety by reference.

These dyes are injected, for example, systemically, and laser-induced fluorescence can be used by endoscopes to detect sites of cancer which have accreted the light-activated dye. For example, this has been applied to fluorescence bronchoscopic disclosure of early lung tumors (Doiron et al., *Chest* 76:32, 1979, included herein by reference; and references cited above).

It is known that dyes can be attached to antibodies for a more specific binding to certain tissues and cells, including malignant and normal cells, depending upon the discriminatory power of the antibodies in question. In cancer, such labeled antibodies have been used in flow cytometry and in immunohistology to stain malignant cells with many different kinds of anticancer antibodies, as described, for example, in Goding, *Monoclonal Antibodies: Principles and Practice*; London/New York, Academic Press, 1983; Ferrone and Dierich, eds., *Handbook of Monoclonal Antibodies*; Park Ridge, N.J., Noyes Publications, 1985; Wick and Siegal, eds., *Monoclonal Antibodies in Diagnostic Immunohistochemistry*; New York/Basel, Marcel Dekker, 1988, incorporated herein in their entirety by reference. Fluorescent and other chromagens, or dyes, such as porphyrins sensitive to visible light, have been used to detect and even treat lesions by directing the suitable light to the tumor or lesion (cited above). In therapy, this has been termed "photoradiation, phototherapy, or photodynamic therapy (Jori and Perria, eds., *Photodynamic Therapy of Tumors and Other Diseases*, Padua: Libreria Progetto, 1985; van den Bergh, *Chem. Britain* 22:430, 1986).

Monoclonal antibodies have been coupled with photoactivated dyes for achieving a photodetection or photocopy (Mew et al., *J. Immunol.* 130:1473, 1983; idem., *Cancer Res.* 45:4380, 1985; Oseroff et al., *Proc. Natl. Acad. Sci. USA* 83:8744, 1986; idem., *Photochem. Photobiol.* 46:83, 1987; Hasan et al., *Prog. Clin. Biol. Res.* 288:471, 1989; Tatsuta et al., *Lasers Surg. Med.* 9:422, 1989; Pelegrin et al., *Cancer* 67:2529, 1991 all incorporated in their entirety herein by reference). However, these earlier studies did not include use of endoscopic imaging and/or therapy or biopsy applications, especially with the use of antibody fragments or subfragments.

Further, there is a need in the art to utilize antibodies and antibody fragments that provide superior targeting specificity and affinity but which are cleared quickly and naturally through the kidneys or which can be cleared quickly with clearing agents, so that targeting can be effected within 48 hours.

A need continues to exist for simple methods which permit enhanced resolution to be achieved for close range intraoperative, intravascular, and endoscopic lesion detection, biopsy and therapy.

A need also exists for improved methods for detection and therapy of tumors.

A need also exists for methods to enable a clinician to intraoperatively, laparoscopically, intravascularly or endoscopically detect and treat non-malignant pathological lesions.

A need further exists for methods to accurately locate lesions in a patient to guide the biopsy implement to the lesion during a biopsy procedure.

OBJECTS OF THE INVENTION

A principal object of the present invention is to provide methods for close-range intraoperative, laparoscopic intravascular, and endoscopic detection of tumors whereby discrimination between tumor and non-tumor tissue is enhanced so that smaller tumors can be detected and appropriate margins can be determined more accurately to permit resection, irradiation, biopsy and/or tumor removal during the procedure and within hours of an injection of labeled protein, whereby surgical, intravascular, laparoscopic, endoscopic evaluation is not delayed.

Another object of the present invention is to provide a method for intraoperative, laparoscopic, intravascular or endoscopic detection, biopsy and therapy of tumors whereby the procedure can be selectively conducted within hours of the injection.

Another object of the present invention is to provide methods for close-range intraoperative, laparoscopic, intravascular, or endoscopic detection and treatment of non-malignant pathological lesions.

Another object of the invention is to provide improved laser therapy, radioimmunotherapy, immunochemotherapy, and/or biopsy procedures for lesions.

Upon further study of the specification and appended claims, further objects and advantages of this invention will become apparent to those skilled in the art.

SUMMARY OF THE INVENTION

These objects can be attained in a method for close-range tumor detection, biopsy and treatment during an operative, laparoscopic, intravascular or endoscopic procedure. The method comprises injecting a patient subject to such a procedure parenterally with an effective amount of a labeled protein, such as an antibody fragment or subfragment, which specifically binds a substance produced by or associated with a targeted tumor. While the procedure is conducted, the accessed interior of the patient is scanned at close-range with a detection means for detecting the presence of the labeled antibody fragment or subfragment. The sites of accretion of the labeled antibody fragment or subfragment are located by detecting elevated levels of the label at such sites with the detection means.

These objects can be attained in a method for close-range intraoperative, laparoscopic, intravascular, and endoscopic tumor detection, wherein a patient subject to such a procedure is injected parenterally with an effective amount of a labeled antibody fragment which specifically binds an antigen produced by or associated with a tumor; the procedure is conducted, preferably, within 48 hours of the injection when unbound radiolabeled antibody fragment in the patient's circulation is reduced at least 50%; the surgically exposed, laparoscopically, or intravascularly or endoscopically accessed interior of the patient is scanned at close range with a label detection means; and the sites of accretion of the labeled antibody fragments are located by detecting elevated levels of label at such sites with the detection means.

In another related aspect, the invention provides a method for close-range detection during an intravascular, operative, laparoscopic, or endoscopic procedure of a non-malignant pathological lesion, wherein a patient subject to the procedure is injected parenterally with an effective amount of an antibody fragment, subfragment or whole antibody, labeled with a labeling agent and which specifically binds an antigen produced by or associated with the lesion, the accessed interior of the patient is scanned at close-range with a detection means for detecting the presence of the labeling agent, and the sites of accretion of the labeled antibody fragments or labeled whole antibody are located by detecting elevated levels of the labeling agent at such sites with the detection means.

The invention also provides a kit suitable for use in an intraoperative, laparoscopic, intravascular, and endoscopic procedure. The kit comprises a first vial containing a sterile injectable preparation for human use comprising an antibody fragment capable of being conjugated with a labeling agent, and a second vial containing a sterile injectable preparation for human use comprising a whole antibody capable of being conjugated with a labeling agent different from the labeling agent of the first vial.

In a related aspect, the invention provides a kit suitable for use in an intraoperative, laparoscopic, intravascular, or endoscopic procedure. The kit comprises a first vial containing a sterile injectable preparation for human use comprising a labeled antibody fragment and a pharmaceutically acceptable carrier, and a second vial containing a sterile injectable preparation for human use comprising a whole antibody labeled with a labeling agent and a pharmaceutically acceptable carrier, wherein the labeling agent of the second vial differs from the labeling agent of the first vial.

In another related aspect, the invention provides an improved method of detection of lesions using endoscopic, laparoscopic, intravascular catheter or surgical procedures. The method comprises injecting a patient to undergo such a procedure with a protein, such as an antibody, antibody fragment or subfragment, labeled with a fluorescent agent or dye, wherein the protein accretes at the lesion; permitting the labeled protein to accrete; and detecting the label with a light source supplied via the endoscope, laparoscope, or intravascular catheter or during the surgical or during the biopsy procedure.

In another related aspect, the invention provides an improved method of detection and treatment of lesions using an endoscope, laparoscopic, or intravascular catheter. The method comprises injecting a patient to undergo such a procedure with an agent capable of detection which preferentially accretes at the lesion; permitting the agent to accrete at the lesion; detecting the agent with a detection means supplied via the endoscope, laparoscopic, or intravascular catheter; and treating the lesion by brachytherapy administered through the endoscope, laparoscopic, or catheter.

In another aspect, the invention provides an improved method of treatment of lesions using endoscopic, laparoscopic, intravascular catheter or surgical procedures. The method comprises injecting a patient to undergo such a procedure with an antibody or antibody fragment labeled with a photoactive agent, wherein the antibody or fragment preferentially accretes at targeted lesions, permitting the labeled antibody or fragment to accrete, and activating the photoactive agent with a light source supplied via the endoscope, laparoscopic, or intravascular catheter or during the surgical procedure.

In another aspect, the invention provides an antibody fragment coupled with a photoactive agent.

In another aspect, the invention provides an improved method of detection and treatment of lesions using endoscopic, laparoscopic, intravascular catheter or surgical procedures.

The method comprises injecting a patient to undergo such a procedure with a first composition comprising either a streptavidin- or avidin-conjugated antibody, biotinylated antibody to be used in conjunction with avidin and biotin, bifunctional antibody, antibody-hapten complexes, or enzyme-conjugated antibody, wherein the antibody is an antibody or antibody fragment which specifically binds a marker produced by or associated with the lesion; after the first composition accretes at the targeted lesion, injecting a second composition which bears a labeling agent capable of detection and which couples with the first composition; and detecting the label with a detection means via the endoscope, laparoscope, or intravascular catheter or during the surgical procedure.

A variation of the above embodiment is when the first composition comprises biotinylated antibody or fragment and the second composition comprises biotin conjugated with fluorescent agent or dye. After the first agent accretes at the targeted lesion and prior to injecting the second composition, the patient is injected with a clearing composition comprising an agent to clear circulating biotinylated antibody or fragment.

In another aspect, the invention provides an improved method for detection of lesions in a patient to undergo an endoscopic, laparoscopic, intravascular catheter or surgical procedure. The method comprises injecting a patient to undergo such a procedure with a first composition comprising an antibody or fragment which preferentially accretes at the lesion and which is labeled with an agent capable of detection with a photoscanning or magnetic resonance imaging device; imaging the lesion with the photoscanning or magnetic resonance device after the labeled antibody or fragment accretes at the lesion; injecting the patient with a second composition comprising an agent capable of detection by an endoscope, laparoscope, intravascular catheter or detection device, such as a hand-held or portable detection means, and which preferentially accretes at the lesion, wherein the agent of the second composition is the same as or different from the agent of the first composition, and allowing the agent to accrete at the lesion; and using the image of the lesion to determine the site for detecting the agent with a close-range detection means provided via the endoscope, laparoscope, or intravascular catheter or during the surgical procedure.

In another aspect, the invention provides an improved method for detection of lesions in a patient to undergo an endoscopic, laparoscopic, intravascular catheter or surgical procedure. The method comprises injecting a patient parenterally with an antibody fragment or subfragment specific to the lesion and which is labeled with a first labeling agent capable of detection using a detection device, and with an indifferent antibody fragment from the same or different species as that used to prepare the specific antibody fragment, the indifferent fragment being labeled with a second labeling agent capable of being independently detected using a detection device, the labeling being so effected that the kinetics and distribution of the labeled specific antibody fragment and the labeled indifferent antibody fragment in the patient are substantially the same during the time period required for detection, wherein at least one of the labeling agents is a photoactive dye; and during the procedure detecting for presence of the labeling agents in the patient with the detection device, the level of activity of the labeled indifferent antibody fragment being used to determine the distribution of background activity due to non-targeted specific antibody fragment, whereby the activity of substantially only the targeted lesion-localized specific antibody fragment is determined and said lesion is thereby detected and localized.

In another aspect, the invention provides an injectable composition, which comprises a substantially monospecific antibody having a specific immunoreactivity of at least 70% to a marker produced by or associated with a lesion and a cross-reactivity to non-lesion-associated antigens of less than 25%; the protein being labeled with a labeling agent capable of detection with a detection device, said labeling being effected to an extent sufficient to reduce the specific immunoreactivity of the antibody by from 5 to 33%; indifferent protein from the same or different species as that used to prepare said specific antibody, said indifferent protein being labeled with a labeling agent capable of independent detection by the detection device; and a pharmaceutically acceptable injection vehicle wherein at least one of the labeling agents is a photoactive dye.

In another aspect, the invention provides an improved method of detection and treatment of lesions. The method comprises injecting a patient with composition comprising a protein conjugated to an agent capable of photoactivated to emit Auger electrons or other ionizing radiation, and, optimally, to an agent capable of detection, wherein the protein conjugate accretes preferentially at the target lesion; and activating the photoactivatable agent and detecting the optional agent capable of detection.

In another aspect, the invention provides an improved method of obtaining biopsy samples, comprising injecting a patient subject parenterally with an effective amount of a labeled antibody fragment or subfragment, which specifically binds an antigen produced by or associated with a lesion, scanning the accessed interior of the patient at close range with a detection means for detecting the presence of the labeled antibody fragment or subfragment, locating the sites of accretion of the labeled antibody fragment or subfragment by detecting elevated levels of the labeled antibody fragment or subfragment at such sites with the detection means, and inserting a biopsy implement into one or more located sites of elevated accretion to obtain a biopsy sample.

In another aspect, the invention provides a method of detection of lesions during an endoscopic, laparoscopic, intravascular catheter, or surgical procedure, comprising injecting a patient who is to undergo such a procedure with a bispecific antibody $F(ab)_2$ or $F(ab')_2$ fragment, wherein the bispecific antibody fragment has a first antibody binding site which specifically binds to an antigen produced or associated with a lesion, such as a tumor- or pathogen-associated antigen, and has a second antibody binding site which specifically binds to a hapten, permitting the antibody fragment to accrete, optionally clearing non-targeted antibody fragments using a galactosylated anti-idiotype clearing agent if the bispecific fragment is not largely cleared from circulation within about 24 hours of injection, injecting hapten, preferably a bivalent hapten, wherein each hapten is a chelate or conjugate of a diagnostic radioisotope such as Tc-99m, I-123, In-11, Ga-67 or the like, or of a MRI image enhancing agent, e.g., Gadolinium ions, Lanthanum ions or the like, or other comparable label, which quickly localizes at the target site and clears through the kidneys, detecting the presence of the hapten by detecting elevated levels of accreted label at the target sites with detection means within 48 hours of the first injection, and conducting the procedure.

DETAILED DISCUSSION

Figure 1:
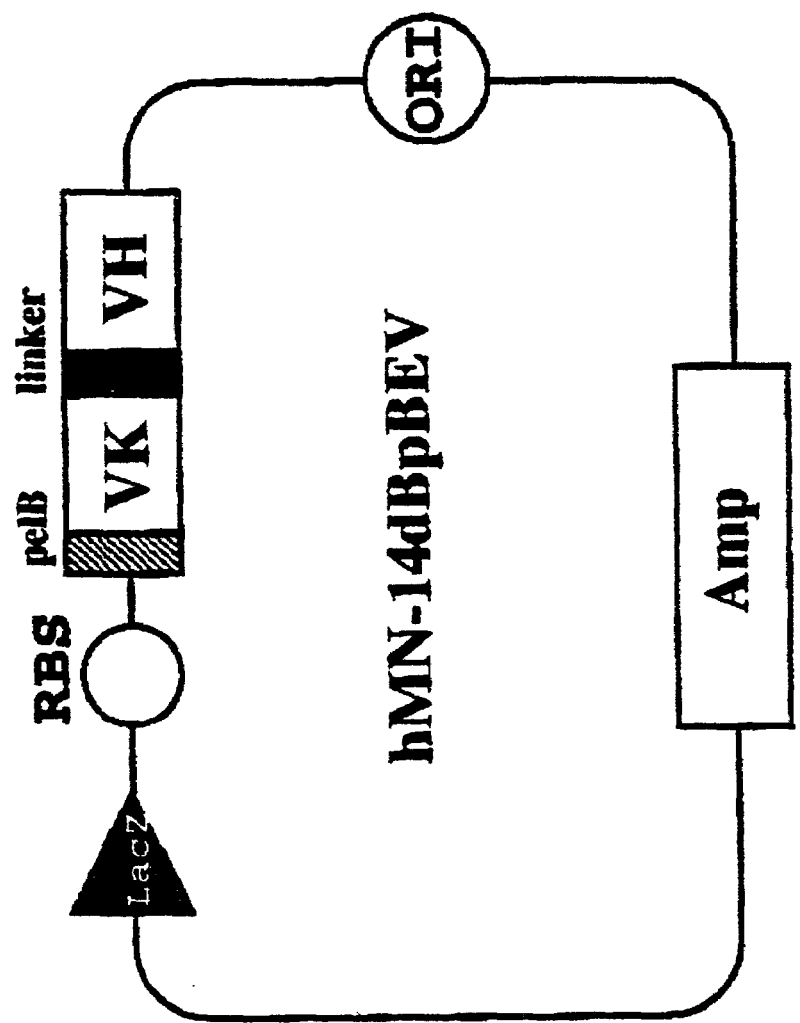
FIG. 1 provides a representation of the expression vector, hMN-14 dBpBEV.

It must be recognized that embodiments of the present invention relate to intraoperative, laparoscopic, intravascular, and endoscopic examination, biopsy and treatment of tissues and/or organs with a labeling agent detecting means capable of close approach to suspected sites of tumor recurrence, metastasis or incomplete removal. As used herein, endoscopic procedures are interpreted to include laparascopic procedures.

Embodiments of the present invention also relate to the intravascular, intraoperative, laparoscopic, and endoscopic examination of lesions with a labeling agent detecting means capable of close approach to suspected sites of the lesions, especially non-malignant pathological lesions. Lesions include cancer, infectious or inflammatory lesions, a non-tumorous or noninfectious inflammation, clots, hyperplasia and atherosclerotic plaques.

The methods of the present invention do not require processing of images, both target-specific and non-target-specific. Rather, one embodiment enables a surgeon or clinician, through the use of, e.g., an intraoperative, laparoscopic, intravascular probe or an endoscope, to scan areas of suspected tumor growth relatively quickly and use the level of radiation to more precisely discriminate tumor tissue from non-tumor tissue and thereby more precisely define tumor borders for surgical resection or diagnostic evaluation, or for laser or radiation therapy, including brachytherapy and external beam therapy, or for improved biopsy procedures.

Other embodiments enable the intravascular, intraoperative, laparoscopic, or endoscopic detection means to be similarly used to define and treat lesions, especially non-malignant pathological lesions.

This general approach can be applied to all endoscopically, including laparoscopically, and even intravascularly approachable lesions or structures in the body.

Antibody fragments or subfragments that specifically bind an antigen produced by or associated with a lesion are useful in the present invention. Divalent single chain antibody fragments or subfragments with a molecular weight of 85,000 daltons or less are preferred. The molecular weight can be 65,000 daltons or less, 55,000 daltons or less or 50,000 daltons or less. The fragment or subfragment can be monospecific or bispecific.

Additionally bispecific antibody $F(ab)_2$ or $F(ab')_2$ fragments, wherein the bispecific antibody fragment has a first antibody binding site which specifically binds to an antigen produced or associated with a lesion, such as a tumor- or pathogen-associated antigen, and has a second antibody binding site which specifically binds to a hapten, can be used in the claimed procedures. If clearance is not sufficiently rapid, e.g., within about 24 hours, a galactosylated anti-idiotype clearing agent can be used to effect rapid clearance.

The use of protein-conjugates of light-sensitive dyes, especially of antibody fragments for imaging and fragments or intact antibodies, preferably of human or humanized forms, for optimization of early and sensitive tumor and other lesion detection or phototherapy in various structures of the body, particularly those reached by endoscopes or various intravascular or extravascular catheters, is preferred.

Further, in order to alleviate nonspecific targeting, which may be experienced at times in some embodiments of the present invention, with such macromolecules as immunoglobulins, a method of controlling nonspecific antibody targeting, comprising the combination of a specific antibody and a nonspecific antibody, or fragments thereof, each labeled with a different dye that is distinguishable from the other agent's dye by photodetection methods, has now been developed. It is further shown that the preferred localizing, specific antibody or fragment, can be dual-labeled with an isotope and a dye, either for simultaneous or separate detection, as desired by the observer. The antibody or antibodies can be injected systemically with at least one dye attached, thus permitting different colors to be developed by photoactivation an viewed in the same endoscope by alternating the nature of the light being delivered and collected for viewing. Such multipurpose viewing endoscodes have been described already, as for example in Hirano et al., *Lasers in the Life Sciences* 3(2): 99, 1989, and in the van den Bergh citation above, both incorporated in their entirety herein by reference, but not in relation to antibody conjugates. A poster presented recently at the Seventh International Conference on Monoclonal Antibody Immunoconjugates for Cancer, San Diego, Calif., Mar. 4–7, 1992, by Folli et al., claimed that a patient injected with a CEA monoclonal antibody conjugated with fluorescein R showed green fluorescence of a rectal tumor observed by fluorescence rectosigmoidoscopy, and claimed this demonstrated the feasibility of photoimmunodiagnosis. Since such tissues are known to have autofluorescence (as noted in the articles cited above, e.g., van den Bergh, 1986), it is not verified that this fluorescence is due to the fluorescing conjugate, and the use of whole immunoglobulin delayed imaging until background activity cleared.

In an embodiment of the present invention, more rapid endoscopic and laparoscopic imaging and detection are possible because of the use of antibody fragments and subfragments conjugated with suitable light-activated dyes. This is also the case for light transmitted by intravascular catheters, both for detection and therapy of intravascular and perivascular lesions, either malignant or nonmalignant.

The use of whole immunoglobulins, even the smaller IgG forms, require sufficient time to clear from background, nonspecific organ targeting. This often constitutes a delay of considerable time (usually 2 or more days) between injection of the chromogenic antibody and imaging of the localized dyes, which is not unlike the problems experienced in antibody imaging by external scintigraphy (radioimmunodetection).

It has now been discovered that the dyes and isotopes used for conjugation to proteins, especially antibodies, for lesion detection can be more effective, faster, and safer when fragments or subfragment forms are deployed. Both monovalent and divalent antibody fragments and subfragments are useful in the present invention. This rapid targeting thus permits the use of both short-lived and long-lived isotopes, or dyes of low and high stability after conjugation, since the detection method can be employed within a few hours of the administration of the new labeling agent(s).

Still another method to rapidly and selectively target a detecting agent by such ionizing and nonionizing radiation is by means of antibody pretargeting procedures, such as, for example, streptavidin- or avidin-conjugated antibodies, biotinylated antibodies in conjunction with avidin and biotin, bifunctional antibodies, antibody-hapten complexes, or enzyme-conjugated antibodies, reviewed in Paganelli, Nucl. Med. Commun. 12:211, 1991, incorporated herein in its entirety by reference.

In addition to delivering radiation to tumors by such 2- and 3-step procedures, the methods can be used to achieve high target/nontarget ratios for intraoperative, endoscopic, and intravascular detection and therapy of tumors and other lesions, including the use of photoradiation for tumor and lesion detection and therapy by endoscopic and intravascular probes within scopes and catheters. The use of light and porphyrins in cancer therapy has been reviewed by the references already cited above.

When endoscopes are used to deliver the nonionizing radiation for therapy of the dye-containing tumors, or for the detection of tumors by fluorescence endoscopy, the procedures are limited to lesions that are accessible to the exciting light and to the detection of the emitted fluorescence, such as in the oral cavity, trachea, bronchi, esophagus, colon, rectum, bladder, vagina, uterus, and other body cavities by use of laparoscopes. Use of light-bearing catheters inserted through veins or arteries enables a more extensive application, especially into organs that are currently examined by intraarterial radiological procedures. Therapeutic applications of antibodies conjugated with light-activating dyes can also be achieved by delivering the nonionizing radiation via such intravascular catheters, particularly in cases where there is a pathological blockage, such as in atherosclerotic plaques or intravascular thrombi or emboli.

This invention also includes the therapeutic use of proteins, especially a bifunctional antibody or antibody fragment, conjugated to agents which can be photoactivated to emit Auger electrons or other ionizing radiation, and, optimally, to agents capable of detection. After the conjugate accretes at the targeted site, activating means and an optional detection means are provided. Agents capable of photoactivation include halogenated compounds, such as halogenated pyrimidines, and certain stable elements, such as iodine and indium. The activating means include monochromatic x-rays, especially those emitted in an energy range of 20–70 keV, more preferably 30–40 keV. The 2- and 3-step procedures disclosed above can be used to deliver agents which can be photoactivated to the targeted sites. These embodiments may apply to intraoperative and endoscopic as well as more generalized uses.

Another goal of an embodiment of the invention is the achievement, as early as possible, of a high target/nontarget ratio of the dye, so that the photoradiation procedure can be instituted before the loss of the dye in the tumor due to instability of the conjugate or because of high autofluorescence in surrounding normal tissues. By using an intravascular catheter, one can now deliver nonionizing radiation to most structures in the body which are accessible to an intravascular catheter. In terms of a rapid method of targeting the dye to a tumor or lesion, it is now discovered that the preferred method is the use of antibody fragments and subfragments as the delivery vehicle of the dye (as a chromophore conjugate) or to use a pretargeting system, such as a 3-step biotin-avidin procedure. In the latter, for example, the biotinylated antitumor antibody is injected parenterally. After sufficient time for the reagent to localize to tumor optimally, such as after about 24 hours and up to about 7 days, but more preferably after 48 hours and before 96 hours, a dose of cold (unlabeled) avidin is given parenterally, followed at 24–96 hours later by a biotin derivative labeled with the detection or therapy isotope or with a suitable photoirradiation dye. The radioactive biotin can be given for detection of lesions intraoperatively, laparoscopically, or endoscopically, or biotin conjugated with a chromophore can be given for tumor/lesion detection and/or therapy by a laparoscope, an endoscope or an intravascular catheter. A description of the 3-step system for targeting carcinoembryonic antigen in tumors, using biotin labeled with In-111, has been described by Paganelli et al., Cancer Res. 51:5960, 1991, incorporated herein by reference. Such pretargeting methods have not been described previously for improved endoscopic and/or intravascular detection and/or therapy of cancer and other pathological lesions. Bispecific pretargeting methods are also contemplated, such as those disclosed in U.S. Pat. Nos. 5,256,395 and 5,274,076, and Rouvier et al., Hormone Research, 47:163–167, 1997, incorporated herein in their entirety by reference, but with the added improvement of rapid clearance, optionally with a galactosylated anti-idiotype clearing agent, thereby permitting injection of an imaging hapten and localization of the lesion within 48 hours. A suitable galactosylated anti-idiotypic antibody is described in U.S. application Ser. No. 08/486,166 and U.S. Pat. No. 4,859,449, both of which are incorporated herein by reference.

It has also been discovered that more effective detection and therapy can be achieved with combinations of agents and procedures involving photodynamic detection and therapy, with or without the use of antibody conjugates, and radioimmunotherapy and/or chemoimmunotherapy. Photodynamic therapy has been used in combination with radiation therapy and chemotherapy in cancer patients (Hayata and Dougherty, 1984, cited above), but combining photodynamic therapy with radioimmunotherapy and/or chemoimmunotherapy is even more effective, since the isotopes or drugs conjugated to tumor-seeking antibodies are more specifically effective than external-beam irradiation or free-drug chemotherapy. The methods and agents for radioimmunotherapy and for chemoimmunotherapy are described in patents and applications, such as, U.S. Pat. No. 4,331,647, U.S. Pat. No. 4,818,709, U.S. Pat. No. 4,348,376, U.S. Pat. No. 4,361,544, U.S. Pat. No. 4,444,744, U.S. application Ser. No. 07/182,623, referred to as the "Goldenberg" patents and "Hansen" application, incorporated herein by reference.

An improved method of cancer therapy is achieved when the photodynamic therapy involves photosensitive agents conjugated to tumor-seeking antibodies combined with radioimmunotherapy and/or chemoimmunotherapy, since these all entail more specific cancer therapy modalities that involve higher therapeutic indices as compared to conventional therapeutic modalities.

General methods of labeling antibodies with fluorochromes are known in the art, and can be found, for example, in Weir, ed., Handbook of Experimental Immunology, Vol. 1, Chapter 28, pp. 28.1–28.21, Oxford, Blackwell Scientific, 1986, incorporated herein in its entirety by reference. For therapeutic purposes, the delivery of high numbers of photoactivating agents to the lesions (malignant and nonmalignant) is critical. Increasing the number of photoactivating molecules attached to the immunoglobulin can affect the antibody's immunoreactivity and, in turn, targeting properties, and usually requires that fewer than 10 such molecules be conjugated to the immunoglobulin. Another requirement is to attach the photoactivating molecules away from the antigen-binding region of the antibody, so as not to hinder the antibody's binding region of the antibody, so as not to hinder the antibody's binding and targeting properties. Both of these requirements are met by use of the aminodextran conjugation method described by Shih et al. in U.S. Pat. No. 5,057,313, incorporated herein by reference. This method permits high numbers of fluorochromes and other light-activating agents to be conjugated to the carbohydrate region of the antibody, away from the antigen-binding sites, usually more than 20 molecules per IgG molecules, and sometimes considerably more.

Previously, Oseroff et al. (*Proc. Natl. Acad. Sci. USA* 83:8744, 1986) used a photosensitizer, chlorine, conjugated in high numbers to antibody via a dextran linkage, and showed photodestruction of human T-cell leukemia cells in vitro. In this circumstance, light could be delivered to the leukemic cells in culture. However, leukemic cells in humans are not accessible to such phototherapy in their usual reservoirs in the body, so it is not readily apparent how these leukemic cell culture experiments would be extrapolated to the human situation. Indeed, in vivo experiments in animals have shown that photodynamic therapy affects the vascularization of tumors by reducing blood flow (Doiron and Gomer, eds., *Prog. Clin. Biol. Res., p.* 170; New York, A. R. Liss, 1984). Indeed, van den Bergh (cited above) has cautioned "possible extrapolation of PDT (photodynamic therapy) results from in vitro experiments to the situation in vivo." Similarly, it is difficult to extrapolate from animal experiments to the clinic, since it is well known that rodent models do not bear the same distribution of target tumor-associated antigens in their blood and tissues as is true for humans, and that the tumor uptake of antibody conjugates is hundreds to thousands and more higher than in humans.

The procedures of intraoperative detection involving the methods and reagents described herein can be combined optimally with external imaging by radioimmunodetection (RAID), using preferably $^{99m}$Tc-, $^{111}$In-, or $^{123}$I-labeled antibody fragments or subfragments, and performing a scanning of the patient prior to surgery, preferably within 24 hours of surgery. The RAID study provides the surgeon with information regarding sites of abnormal radioactivity of putative disease, which enables the surgeon to focus in on such areas with the intraoperative probe during surgery or laparoscopy. Likewise, the RAID study can be advantageously performed prior to the fluorescence endoscopy or intravascular catheterization study, in order to better define areas of disease. More versatile agents can also be used, whereby an anticancer antibody fragment is labeled with both an imaging and detection isotope (e.g., $^{99m}$Tc) and with a fluorescent dye, or where a bifunctional or bispecific antibody is used, one arm directed to the lesion and labeled with a suitable radionuclide, and the other arm directed to a hapten conjugated with a fluorescent dye, or to a hapten to which a fluorescent dye can be bound after injection parenterally. In another combination, one arm of a bispecific F(ab)$_2$ or F(ab')$_2$ antibody fragment is directed to the lesion, e.g., a tumor, and the other arm to a hapten, the hapten to be administered in a subsequent step, after rapid clearance. Other combinations of an isotopic probe and a fluorescent (or chromophore) probe, as apparent from 2- and 3-step targeting methods (cited above), can be used to allow for contemporaneous use of nonionizing and ionizing radiation probes for intraoperative, endoscopic, laparoscopic, and intravascular detection of pathological lesions.

This principle is also applicable to therapy, where combinations of modalities are more effective than one method alone. For example, systemic radioimmunotherapy or chemoimmunotherapy can be advantageously given before or after photoactivated therapy (via an endoscope, laparoscope, or intravascular catheter after deposition of the chromophore by conventional injection or via an antibody conjugate), whereby the radioimmunotherapy or chemoimmunotherapy are working in combination or synergistically with the phototherapy. These variations again can include 2- and 3-step pretargeting procedures, including bispecific antibodies, in order to achieve higher target/nontarget ratios for the delivery of the chromophore or of the radiation to the tumor or pathological lesion.

Still another improvement in cancer therapy is the use of endoscopes, including laparoscopes, and catheters involving isotopically- or photosensitizer-conjugated anticancer antibodies in combination with brachytherapy involving the implantation of radioactive pellets by means of a scope or catheter.

The isotopically or photosensitizer-conjugated antibody can serve as a detection method for directing the application of brachytherapy, or also as a therapy in conjunction with brachytherapy.

Such brachytherapy is conducted in situations almost identical to the use of photodynamic therapy, so it is an improvement to use photodynamic therapy, with or without conjugating the photosensitizer to a tumor-seeking antibody (but preferably with an antibody conjugate), together with brachytherapy, such as radon-222, iodine-125, cesium-137, cobalt-60, and iridium-192.

It is preferred to use brachytherapy in combination with laser therapy, external beam radiation, chemoimmunotherapy and/or radioimmunotherapy, since higher antitumor doses with lower host side effects are achieved. Combinations of brachytherapy with Nd-YAG laser therapy in lung carcinoma have already been reported (Allen et al., *Am. J. Surg.* 150:71, 1985; Schray et al., *Int. J. Radiat. Oncol. Biol. Phys.* 11:403, 1985—both incorporated in their entirety herein by reference), as well as the general use of intraluminal brachytherapy in lung cancer by Nori et al., *Surg. Clin. N. Amer.* 67:1093, 1987, incorporated herein in its entirety by reference. More effective therapy is now achieved by combinations of the various modalities of brachytherapy, laser therapy, photodynamic therapy, radioimmunotherapy, and chemoimmunotherapy, particularly with the application of tumor-seeking antibodies conjugated with therapeutic modalities.

The short-range detection method according to the invention may use a detector capable of detecting radiation emitted from or color provided by a label bound to the protein.

The label may be alpha, gamma, beta, positron, fluorescence or any other detectable ionizing or nonionizing radiation which can be produced by a convenient label capable of attachment to a protein, preferably an antibody or antibody fragment. For example, a gamma detector suitable for such a function has been reported by Aitken et al., *Dis Colon & Rectum,* 27, 279–282 (1984). These authors describe a hand-held gamma probe using a cadmium telluride scintillation crystal, a preamplifier and an amplifier with a digital readout displaying the radioactive counts (Radiation Monitoring Devices, Watertown, Mass.). The scintillation crystal is housed in a 16-mm diameter lead collimator with a 4-mm aperture. This device has been shown to detect tumor with radiolabeled antibody injected intraperitoneally, and to distinguish tumor tissue from nearby non-tumor tissue. However, the disclosed method requires long delays between injection and probing, with unpredictable results obtained from patient to patient.

It will be apparent to the ordinary skilled artisan that other detection means can be used and that the detector is not limited to gamma radiation.

It will also be apparent that the detector can be made to discriminate between radiolabeling agents of different energies of incident radiation, e.g., between gamma radiation in different ranges within the broad 20–1,000 keV range which is used for gamma scintillation counters and/or between alpha-, gamma-, and beta-radiation emitted by different radiolabeled proteins. Thus, the invention is not limited by the type of detector used.

A scintillation crystal can be mounted on the end of a fiber optic cable and its optical response to incident gamma radiation can be transmitted to a photomultiplier and associated circuitry through the optical fiber. This can reduce the size of the detector to be compatible with use in conjunction with an endoscope or intravascular catheter. The endoscope or catheter can be shielded to serve as a collimator, where necessary, and/or fitted with a window at a known distance from its terminus, with the scintillation crystal housed therein.

Various other modifications and adaptations of the foregoing will be readily apparent to the ordinary skilled artisan, in light of the particular needs of the situation. However, the method of the present invention is not limited by any specific type of radiolabeling agent detector. Rather, any detector which is capable of detecting the label localized in targeted lesion, tissue or organ can be used.

The detection means can be used in the form of an endoscope, and inserted into a body cavity through an orifice, such as, the mouth, nose, ear, anus, vagina or incision. The term "endoscope" is herein used generically to refer to any scope introduced into a body cavity, e.g., an anally introduced endoscope, an orally introduced bronchoscope, a urethrally introduced cystoscope, an abdominally introduced laparoscope or the like. Certain of these may benefit greatly from further progress in miniaturization of components and their utility to practice the method of the present invention will be enhanced as a function of the development of suitably microminiaturized components for this type of instrumentation.

Highly miniaturized probes which could be introduced intravascularly, e.g., via catheters or the like, are also suitable for use in the embodiments of the invention for localizing and treating tumors and the embodiments for localizing and treating non-malignant pathological lesions, such as, an infarct, including myocardial, atherosclerotic plaque, clot, including thrombosis, pulmonary embolism, infectious or inflammatory lesion, non-tumorous or noninfectious inflammation, or hyperplasia.

In methods of the present invention, techniques useful in imaging applications are adapted for the improved methods of the presentation. Methods of localization and therapy of tumors and lesions, and methods of organ imaging, using radiolabeled antibodies and antibody fragments which specifically bind markers produced or associated with tumors, lesions and normal organs or tissue, have been disclosed, inter alia, in U.S. application Ser. No. 07/694,977, filed May 6, 1991 and U.S. Pat. Nos. 4,331,647; 4,348,376; 4,361,544; 4,444,744; 4,460,561; and 4,624,846, the disclosures of all of which are incorporated herein their entireties by reference (hereinafter, "the Goldenberg patents"). These references also disclose antibodies and antibody fragments for use in the foregoing methods, together with methods for obtaining them and for radiolabeling them with appropriate radionuclides.

Antibody fragments useful in the present invention are F(ab')$_2$, F(ab)$_2$, Fab', Fab, Fv and the like, including hybrid fragments. Also useful are any subfragments retaining the hypervariable, antigen-binding region of an immunoglobulin and having a size similar to or smaller than a Fab' fragment. This will include genetically engineered and/or recombinant proteins, whether, single-chain or multiple-chain, which incorporate an antigen binding site and otherwise function in vivo as targeting vehicles in substantially the same way as natural immunoglobulin fragments. Such single-chain binding molecules are disclosed in U.S. Pat. No. 4,946,778, which is hereby incorporated by reference. Fab' antibody fragments may be conveniently made by reductive cleavage of F(ab')$_2$ fragments, which themselves may be made by pepsin digestion of intact immunoglobulin. Fab antibody fragments may be made by papain digestion of intact immunoglobulin, under reducing conditions, or by cleavage of F(ab)$_2$ fragments which result from careful papain digestion of whole Ig. The fragments may also be produced by genetic engineering.

An Fv fragment is approximately 25,000 daltons and is the smallest fragment produced from IgG and IgM that contains a complete antigen binding site. Fv fragments have the same binding properties and similar three-dimensional binding characteristics as Fab (50,000 daltons). The $V_H$ and $V_L$ chains of the Fv fragments are held together by noncovalent interactions. These chains tend to dissociate upon dilution, so methods have been developed to crosslink the chains through glutaraldehyde, intermolecular disulfides or a peptide linker. However, the divalent single chain antibodies of the present invention are produced by recombinant techniques.

Divalent single chain antibody fragments or subfragments, such as (sFv)$_2$ and (sFv')$_2$, are preferred antibodies to utilize in the methods of the present invention. The (sFv)$_2$ and (sFv')$_2$ antibody fragments have two antigen binding sites and provide better targeting and affinity to the antigen than monovalent antibodies with one antigen binding site, such as Fab', Fab, Fv or Fv'. The (sFv)$_2$ and (sFv')$_2$ antibody fragments are preferred because they have a lower molecular weight than F(ab')$_2$ fragments (IgG—110,000 daltons) resulting in faster clearance from the body. The fragments, (sFv)$_2$ and (sFv')$_2$, are similar in molecular weight to the Fab' (55,000 daltons) but are divalent rather than monovalent, thus providing an antibody fragment with better affinity and specificity to the lesion-associated antigen. An (sFv')$_2$ fragment has a cysteine at the end of each Fv (Fv'). Each is independently expressed recombinantly, e.g., in E. coli, and two Fv' fragments are chemically joined through a disulfide bond. See, e.g., Tai et al., Cancer Research (Suppl.) 55:5983s–5989s, 1995; and Zhu et al., Biotechnology, 14:192–196, 1996, both of which are incorporated herein by reference.

A F(ab)$_2$ or F(ab')$_2$ fragment is too large to be filtered through the glomerular basal membrane. This divalent fragment must be catabolized elsewhere; e.g. in the liver, and the smaller breakdown products are excreted via the kidneys. Without the use of a clearing agent, the clearance of this fragment takes longer than the divalent single chain fragments of the present invention and can unduly delay other procedures.

The divalent single chain antibody fragments or subfragments useful in the present invention have a molecular weight of 85,000 daltons or less, which is about the upper limit for filtration by the kidneys. The molecular weight of these antibody fragments can be 65,000 daltons or less, 55,000 daltons or less or 50,000 daltons or less. The fragment or subfragment can be monospecific meaning that the two antigen binding sites are directed to epitopes on one antigen, such as the following antibodies, MN14, LL2, MA5, and RS7 or they can be bispecific where each antigen binding site binds to an epitope on a different antigen, such as hMN14/hMu9 (h is an abbreviation for human). The methods of making and the description of these antibodies are disclosed in U.S. Ser. Nos. 08/690,102 and 08/318,157, which are both incorporated herein in their entirety by reference.

However, bispecific F(ab)$_2$ and F(ab')$_2$ divalent fragments also can be used, wherein one binding site is specific to a tumor or lesion and the second binding site is specific to a hapten; e.g., a diagnostic agent, which is radiolabeled, fluorescent labeled, or Auger generating labeled hapten. In order to effect location of the target site within 48 hours, the non-targeted bivalent F(ab)$_2$ and F(ab')$_2$ fragments, if not significantly cleared (at least 50% reduction in circulating level, preferably 85% or more) within about 24 hours, are cleared from circulation using any one of several known clearing agents. In a preferred embodiment, an anti-idiotype antibody is used, preferably one which specifically binds the target binding site of the bispecific fragment. The anti-iodiotype antibody is preferably modified by conjugation to galactosyl residues for more rapid uptake in the liver. Alternatively, this bispecific antibody can be biotinylated and clearance can be effected with avidin or streptavidin. A further alternative is the use of a second antibody clearance. For specifics on this type of clearance methods, see U.S. Pat. No. 4,624,846, Goldenberg, which is herein incorporated by reference in its entirety.

The following procedures provide examples of the construction of single chain Fv homodimeric and heterodimeric diabodies.

Single-Chain Antibody (scFv) for hMN-14: In the original design for hMN-14 scFv, the VK domain is linked at its C-terminus to the VH by a 15-mer peptide linker having the sequence (GGSGS)$_3$. The DNA sequence encoding the hMN-14 scFv is cloned into a pET-related bacterial expression vector (Novagen, Madison Wis.), in which the gene encoding hMN-14 scFv is driven by a T7 promoter. The scFv is obtained by solubilization and refolding of inclusion body proteins from the host *E. coli* BL21 (λDL3)(Studier and Moffatt, *J. Mol. Biol.* 189:113, 1986) as described (Buchner et al., 1992). Properly refolded proteins are purified by sequential ion exchange chromatography on Mono Q (Pharmacia) followed by size exclusion chromatography on a TSK G3000SW (TosoHaas) column. The scFv is purified as a monomeric protein with immunoreactivity comparable to that of hMN-14 Fab' fragment.

Design and Construction of Bacterial Express Vector for Homodimeric Diabody for hMN-14: A pUC19-based vector, hMN-14pBEV (Leung et al., *Cancer Res.* (suppl.) 55:5968s–5927s, 1995), containing the sequence encoding the Fab fragment of hMN-14, is used as the template for the PCR-amplification of the hMN-14 VK and VH sequence. The PCR-amplified VK sequence is linked at its C-terminus to the VH sequence via a five amino acid linker, GGPGS. The resultant protein, if expressed, should have a configuration of VK-linker-VH. Other linkers, such as those derived from the N-terminus of the human CK domain (RTVAA, RTVAAPS or RTVAAPSHFT) can also be used. This shortened linkers are designed to prevent intra-chain and to encourage inter-chain cross-over pairing of VK and VH. Alternatively, the diabody can be aligned in the configuration of VH-linker-VK.

To construct the diabody expression vector, the DNA sequence encoding the Fab for hMN-14 is spliced out from the bacterial expression vector hMN-14pBEV by restriction digestion, and is replaced by that encoding the diabody. A PelB sequence is joined in-frame to the N-terminus of the diabody gene to allow transportation of the translated product into the bacterial periplasm for proper folding and disulfide-linkage formation (Better et al., *Science* 240:1041-1043, 1988; Skerra & Plückthun, *Science* 240:1038–1041, 1988). The diabody gene is driven by an inducible LacZ promoter. The structure of the final expression vector, hMN-14 dBpBEV, is shown in FIG. 1.

Figure 2:
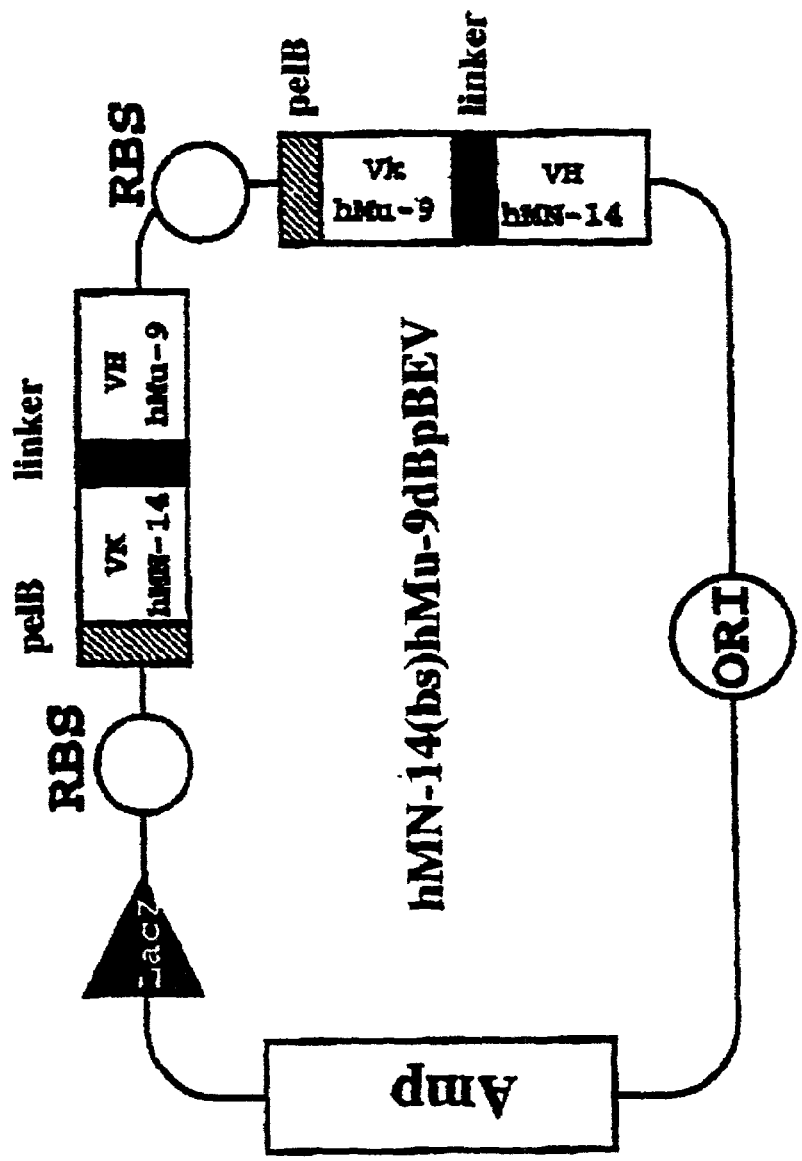
FIG. 2 provides a representation of the expression vector, hMN-14 (bs)hMu-9 dBpBEV.

Design and Construction of a Bacterial Expression Vector for a Bispecific Diabody for hMN-14 and hMu-9: The V-region sequences for a colon-specific antigen-p antibody, Mu-9, has been elucidated (Krishnan et al., *Cancer* (suppl.) 80:2667–2674, 1997). A humanized Mu-9 (hMu-9) antibody was derived and shown to retain full immunoreactivity as compared to that of murine Mu-9. The expression vector for hMu-9, designated as hMu-9KpdHL2, is used as the template for the PCR-amplification of its V-gene sequences. Unlike the homodimeric expression vector for hMN-14 diabody, the expression vector for the bispecific diabody contains a dicistronic gene sequences with the configuration: VL(hMN-14)-linker-VH(hMu-9), aligned in series with VL(hMu-9)-linker-VH(hMN-14) (FIG. 2). The linker is composed of the sequence GGPGS. The shortened linker is designed to prevent intra-chain pairing of VK and VH and to ensure cross-over inter-chain pairing. Both gene sequences are fused in-frame with a PelB sequence at their N-terminus. The dicistronic gene is cloned into the hMN-14pBEV vector, replacing the sequence encoding the Fab fragment. The final expression vector is designated as hMN-14(bs)hMu-9dBpBEV (FIG. 2).

Expression and Purification of Monospecific and Bispecific Diabodies: CsCl-purified DNAs of hMN-14dBpBEV and hMN-14 (bs)hMu-9dBpBEV bacterial expression vectors are used to transform the *E. coli* BMH71-18mutS (CLONTECH, Palo Alto, Calif.). Transformants are grown overnight at 37° C. in 2xTY supplemented with 55 mM glucose and 100 μg/ml of ampicillin. The overnight culture is pelleted, washed twice with 2xTY, and resuspended with prewarmed 2xTY in the presence of 1–5 mM isopropylthiogalactoside. After an induction period of 20–24 h at 37° C., the culture is pelleted. The diabody in the periplasm is released from the cell pastes by osmotic shock facilitated by partial digestion of the cell wall with chicken egg white lysozyme (Carter et al., *Bio/Technology* 10: 163–167, 1992). The diabody is then affinity purified by Staphylococcal protein A chromatography. For the bispecific diabody, the protein A-purified proteins should contain a mixture of bispecific diabody and each of the inactive homodimers. The mixture is subjected to another round of affinity-purification with WI2-column. WI2 is an anti-idiotype antibody specific for MN-14 (Losman et al., 1994). Since none of the two possible homodimers is immunoreactive, all immunoreactive diabodies have to be bispecific.

An additional example of divalent single chain antibody fragments useful in the methods of the present invention are disclosed in Adams et al., *Cancer Research* 53:4026–4034 (1993) and incorporated herein by reference. This publication discloses preparing divalent disulfide-bonded (sFv')$_2$ molecules which exhibit divalent binding characteristics and equivalent binding affinity to parental IgG. These molecules have a molecular weight of 53,000 daltons and remain below the threshold for renal clearance. They are cleared from the blood nearly as rapidly as sFv monomers, apparently without in vivo disruption of the (sFv')$_2$ interchain disulfide bond.

Another useful single chain divalent antibody fragment is disclosed by Haunschild et al., *Antibody, Immunoconjugates, and Radiopharmaceutics*, Vol. 9, No. 2, 111–128 (1995) and incorporated herein by reference. These antibody fragments are bivalent "miniantibodies" based on single chain Fv fragments that are fused via a flexible hinge-region to association domains. This antibody is known as scZIP and is held together by the formation of a parallel coiled coil helix, also termed leucine zipper. These antibodies were found to be cleared through the kidneys somewhat slower than a scFv fragment but much faster than a whole antibody.

A further single chain Fv useful in the presently described methods is described in *Immunology/Preclinical and Clinical Biological Therapy* 1, Abstract #180 by Rajagopal et al., incorporated herein by reference. The disulfide-stabilized (dsFv) fragments of antibodies are more stable than their single-chain counterparts. The heavy and light chains are held together by the conventional peptide linker and cysteines are engineered into the heavy and light chain variable regions so that a disulfide bond is formed between the two chains.

Bispecific divalent single chain antibodies (diabodies) also useful in the present invention are disclosed in Tai et al.1, *Cancer Research* (suppl.) 155:5983s–5989s (1995). The molecular size of these diabodies are less than Fab' when evaluated by molecular sizing gel exclusion (FIG. 3 of the Tai et al. publication).

The antibody may be whole immunoglobulin of any class, e.g., IgG, IgM, IgA, IgD, IgE, chimeric or hybrid antibodies with dual or multiple antigen or epitope specificities. It can be a polyclonal antibody, preferably an affinity-purified antibody from a human or an appropriate animal, e.g., a primate, goat, rabbit, mouse or the like. Monoclonal antibodies are also suitable for use in the present method, and are preferred because of their high specificities. They are readily prepared by what are now considered conventional procedures of immunization of mammals with immunogenic antigen preparation, fusion of immune lymph or spleen cells with an immortal myeloma cell line, and isolation of specific hybridoma clones. More unconventional methods of preparing monoclonals antibodies are not excluded, such as interspecies fusions and genetic engineering manipulations of hypervariable regions, since it is primarily the antigen specificity of the antibodies that affects their utility in the present invention. It will be appreciated that newer techniques for production of monoclonals can also be used, e.g., human monoclonals, interspecies monoclonals, chimeric (e.g., human/mouse) monoclonals, genetically engineered antibodies and the like.

It should be noted that mixtures of antibodies, isotopes, and immunoglobulin classes can be used, as can hybrid antibodies. The hybrids can have two different antigen specificities, e.g., one arm binding to a tumor antigen such as carcinoembryonic antigen and another arm binding to another antigen, e.g., CSAP, or one arm could bind to one epitope on, e.g., carcinoembryonic antigen and the other arm could bind to another carcinoembryonic antigen epitope. The foregoing are merely illustrative, and other combinations of specificities can be envisioned that also fall within the scope of the invention.

Hybrid antibody fragments with dual specificities can be prepared analogously to the anti-tumor marker hybrids disclosed in U.S. Pat. No. 4,361,544. Other techniques for preparing hybrid antibodies are disclosed in, e.g., U.S. Pat. Nos. 4,474,893 and 4,479,895, and in Milstein et al., *Immunol. Today*, 5,299(1984).

Unbound labeled antibody fragments will clear from the patient's circulation quickly and thereby be reduced by at least 50% within 48 hours, preferably 24 hours, more preferably 12 hours, and even more preferably 6 hours, after injection. It is preferable that the reduction be at least 75%, more preferable 85%.

Unbound whole antibody will clear from the patient's circulation and the amount of unbound whole antibody reduced by no more than 50%, in no less than 48 hours.

The labeling agents useful in the methods of the present invention include isotopic or non-isotopic labels, such as fluorescent agents and other dyes, etc. Such labels are well known to these skilled in the art.

The radioisotope selected by one skilled in the art to radiolabel the fragment will have a half-life to complement binding time of the fragment to the antigen.

The labeling agent for the antibody fragment is preferably an isotope with a gamma radiation emission peak in the range of 20–500 keV, primarily because the state of the art for radiation detectors currently favors such radiolabels.

Suitable such radioisotopes for antibody fragments include, e.g., Iodine-123, Indium-113m, Gallium-68, Rheniua-188, Technetium-99m, and Fluorine-18. Preferred isotopes are Technetium-99m and Iodine-123. However, isotopes with longer half-lives can also be used. Beta emitters and position emitters also can be used.

The labeling agents used in the methods of the present invention include isotopic or non-isotopic labels, such as fluorescence, etc. Such labels are well known to these skilled in the art and are disclosed above.

The radioisotope selected by one skilled in the art to radiolabel the whole antibody should have a half-life which complements the antibody being used.

Examples of suitable radioisotopes for whole antibodies include Indium-111, Iodine-125, Iodine-131, and Gallium-67.

In a method of the present invention wherein more than one isotope is used, the two radiolabels should be of sufficiently different energies or sufficiently different half-lives to be separately detectable with the detection means. Suitable such pairs of radioisotopes include, e.g., Iodine-131/Iodine-123, Iodine125/Technetium-99m and the like.

U.S. Pat. No. 4,782,840 discloses antibodies specific for neoplastic tissue and radioisotopes useful in a surgical procedure wherein an animal suspected of containing neoplastic tissue is surgically accessed and the tissue therein examined visually and by palpation for evidence of neoplastic tissue. The disclosed antibodies radiolabeled with the disclosed radioisotopes are injected into the patient at least 7 days, and preferably 7–21 days, prior to the surgery so that during the surgery a probe may used to determine the presence of radiolabeled antibody bound to neoplastic tissue.

The antibodies and radioisotopes of that reference, hereby incorporated by reference, are useful in the methods of the present invention wherein an injection of a radiolabeled antibody is administered.

In the method of the present invention wherein intravascular, intraoperative, laparoscopic, or endoscopic procedures are used to detect and treat lesions and an injection is made of only one labeled protein, any label disclosed herein as useful for labeling either fragments or whole antibodies may be used.

Suitable radioisotopes include, e.g., Cobalt-57, Iodine-131, Iodine-123, Iodine-124, Iodine-125, Iodine-126, Iodine-133, Bromine-77, Indium-111, Indium-113m, Copper-67, Gallium-67, Gallium-68, Ruthenium-95, Ruthenium-97, Ruthenium-103, Ruthenium-105, Mercury-197, Mercury-203, Rhodium-99m, Rhodium-101, Rhodium-105, Selenium-75, Tellurium-121m, Tellurium-122m, Tellurium-125m, Thulium-165, Thulium-167, Thulium-168, Rhenium-186, Rhenium-188, Technetium-99m, Fluorine-18, and Zirconium-97. Preferred are Technetium-99m, Iodine-123, Iodine-125, Iodine-131, Indium-111, and Gallium-67. Examples of beta-emitters are Phosphorus-32, Yttrium-90, Copper-67, Rhenium-186, Rhenium-188 and others.

The probe can be combined with surgical removal of detected tumor or lesions, cells, or tissue, and this is the conventional mode of operation in second-look surgery. Another possibility for such surgery, and especially for endoscopic and laparoscopic procedures, is to combine the probe with a laser device that could use the signal generated by the probe to indicate where laser irradiation should be directed to selectively destroy tumor tissue.

Suitable laser devices, combined with fiber optic transmission, are well known in the art. Representative examples thereof are described, inter alia, in, e.g., Dixon, Lasers in Surgery, in "Current Problems in Surgery", Pgs. 1–65 (Year Book Medical Pubs., Inc. 1984); Fleisher, *Arch. Intern. Med.*, 144, 1225–1230 (1984); Wood et al., *Am. J. Gastroent.*, 80, 715–718 (1985); and Hunter et al., *Am. J. Surg.*, 148, 736–741 (1984). Three types of lasers are currently in fairly widespread use for medical therapy, namely the argon, carbon dioxide and neodymium-YAG (yttrium aluminum garnet) lasers. As noted by Fleischer, Nd-YAG and argon lasers have been used with fiber optic waveguides, although it is likely that further advances in $CO_2$ laser technology will permit its use with fiber optics in the near future.

The foregoing references show that lasers have been used for therapy, in conjunction with endoscopy, both in coagulative and in ablative modes, including their use for tumor therapy. The use of lasers and endoscopy has advantages where surgery is contraindicated. Used in conjunction with the endoscopic procedure according to the present invention, greater precision and mitigation of damage to normal tissue is achieved.

The probe can also be used to provide radiation therapy such as brachytherapy and external beam radiation to the site.

However, it normally will not be possible to optimize scanning in the same way for intraoperative, intravascular or laparoscopic or endoscopic examination as it is for external imaging. Rather, in the event that it is desired to optimize the timing of the procedure, a blood sample can be taken at periodic intervals after injection of the protein and the level of activity of the label in the blood is determined, so that the efficacy of clearance and the level of circulating label can be observed. This will indicate the best time for the surgical, intravascular, or laparoscopic or endoscopic procedure. For example, when the level of circulating label being detected is reduced by at least about 50%, preferably at least about 75%, more preferably by at least about 85%, or even more, the interference of background radiation with the short-range detection process will be minimized, and detection will be enhanced.

The invention provides a kit suitable for use in an intraoperative, intravascular, laparoscopic, or endoscopic procedure.

The kit may comprise a vial containing a sterile preparation for human use comprising an antibody fragment capable of being labeled with an isotopic or non-isotopic agent, and a vial containing a sterile preparation for human use comprising an antibody capable of being labeled with a differing labeling agent.

The kit may also comprises a vial containing a sterile injectable preparation for human use comprising a labeled antibody fragment and a pharmaceutically acceptable carrier, and a vial containing a sterile injectable preparation for human use comprising an antibody labeled with a differing labeling agent and a pharmaceutically acceptable carrier.

The labeled antibody fragment and labeled antibody are each conveniently provided as an injectable preparation for mammalian use, preferably a sterile injectable preparation for human use, preferably comprising: a sterile injectable solution containing an effective amount of the labeled antibody fragment or labeled antibody in a pharmaceutically acceptable sterile injection vehicle, preferably phosphate-buffered saline injection vehicle (PBS) at physiological pH and concentration. Other conventional pharmaceutically acceptable vehicles for parenteral administration may be utilized as required for the site of parenteral administration.

A representative preparation to be parenterally administered in accordance with this invention will normally contain about 0.01 to 20 mg, preferably about 0.05 to 5 mg, of labeled antibody fragment or labeled antibody, in a sterile solution which advantageously also contains, e.g., about 10 mg of human serum albumin (1% USP, Parke-Davis) per ml of 0.04M phosphate buffer (pH 7.4 Bioware) containing 0.9 sodium chloride.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

The biopsy technique of the present invention involves exposing suspicious areas using a scalpel, cutting a representative specimen for tissue analysis by means of histology. Alternatively, in another situation, a special biopsy instrument or a needle probe is used to obtain the tissue sample.

EXAMPLES

Example 1

Intraoperative Tumor Detection

A female patient with a cecal carcinoma recurrence is injected i.v. with Tc-99m-labeled murine monoclonal antibody NP-4 Fab' fragment against carcinoembryonic antigen (CEA) (15 mCi Tc-99m; 1 mg Fab'). The patient is scanned with a gamma camera, producing both planar and single-photon emission computed tomographic images at 3–5 hours later, and the cecal lesion is defined. Without delaying the planned surgery, the patient is brought to the operating room 8 hours after the antibody administration, and undergoes surgery for removal of the cecal tumor and any other sites of involvement in the region. This is achieved by passing a sterile radiation probe over the viscera to identify sites of tumor spread. The probe has a cadmium telluride scintillation crystal, collimator, preamplifier and amplifier, similar to that reported by Aitken et al., op. cit., but is collimated to select energy in the range of 100–160 keV. The counts registered are translated into a digital recording and an auditory signal at a significant increase over background counts. An increase in count ratio and signal of at least 60% relative to non-tumor areas is noted at the cecal tumor site, and extends for a distance of about 3 cm from the gross margins of the tumor. The surgeon removes the tumor and normal-appearing colon extending a distance of about 3.5 cm from the gross margins of the tumor on all sides, at which distance the ratio of counts was not more than 25% higher than the normalized base ratio. Also, a mesenteric lymph node giving at least a 100% increased signal over background is also resected. The resected tissues are fixed in formalin and are found by histopathology to contain carcinoma cells. The colon tumor borders are found to be devoid of cancer invasion. Based upon follow-up of the patient for 7 months, no evidence of local or distant cancer recurrences is found, and the blood CEA titer, which is elevated prior to surgery, has remained within the normal range not exceeding 2.5 ng/ml.

Example 2

Endoscopic Tumor Detection (A) A male patient with a suspected colonic polyp (having a history of recurrent polyps in the colon) is scheduled for a colonoscopy because of a recent positive guaiac test for hemoglobin in his stool, and an elevated blood CEA titer of 12.5 ng/ml. A dose of CEA monoclonal antibody NP-4 F(ab')$_2$ labeled with I-125 by the chloramine-T method (2 mg F(ab')$_2$ with 1.0-mCi I-125) is injected i.v. and 24 hours later, without delaying the planned endoscopic procedure, the patient undergoes endoscopy, using a colonoscope equipped with a radiation detector capable of measuring the radiation emitted by I-125. The detector comprises a cadmium telluride scintillation crystal mounted on the tip of an optical fiber waveguide. The optical fiber is housed within a shielded tube which itself is inserted inside the colonoscope and extends to within about 4 mm of the open end thereof, the remaining length of tubing serving as a collimator. The other end of the optical fiber leads to a photomultiplier, a preamplifier and amplifier, and means to convert the resultant signal to a corresponding auditory signal. The gastroenterologist examining the colon with the colonoscope finds 2 small pedunculated polyps within a distance of 20 and 25 cm from the anal verge, measuring about 1.5 cm and 0.8 cm in diameter, respectively. The radiation detector shows an enhanced signal only over the larger polyp, this signal appearing 1.8 times higher than background activity or the radioactivity over the other, smaller, polyp. Both polyps are removed by means of a loop inserted in the colonoscope, extracted through the scope, and processed for histopathology. It is found that only the one having the high radioactivity signal contains cancer cells; this polyp has an area of adenocarcinoma.

(B) In another case of endoscopy similar to the above, a patient receives a monoclonal antibody to carcinoembryonic antigen (CEA) which is conjugated to dihematoporphyrin ether, DHE (Photofrin II), by an adaptation of the carbodiimide-conjugation method of Mew et al., J. Immunol. 130: 1473, 1983, at a dose of 1.5 mg DUE per kg body weight i.v. The fiberoptic colonoscope used to detect the fluorescence of the agent targeted to a malignant polyp is similar to the fiberoptic bronchoscope described by Profio et al., Adv. Exp. Med. Biol. 193:43, 1985, using a violet krypton ion laser emitting at 410 nm. The fluorescence intensity is converted to an audio signal, whose pitch is related to the signal's intensity by analyzing the fluorescence in a photomultiplier tube. In this case, the malignant polyp at a distance of 15 cm from the anal verge has a ratio of fluorescence to background of 6:1. The polyp of 0.5 cm in diameter is removed via the colonoscope, fixed in formalin, and processed for histopathology. An adenocarcinoma in the stalk of the polyp is found to be present.

Example 3

Intraoperative Tumor Therapy

A woman with ovarian cancer having extensive abdominal spread is injected prior to surgery with a biotinylated preparation of RS7-3G11 monoclonal antibody (3 mg) i.v. Three days later a chase dose of avidin (10 mg) is given i.v. in 2 divided doses 60 minutes apart. Twenty-four hours later, a 1.5 mg dose of biotinylated RS7-3G11 conjugated with DTPA-indium (stable) is injected i.v. The next day, the patient undergoes a resection of all visible and palpable tumors in her abdominal cavity, followed by intraoperative irradiation of the exposed cavity with monochromatic X-rays of 40 keV to destroy micrometastatic cancer spread. At 6 and 9 months later, no evidence of disease is present, and the patient's blood CA-125 titer is within the normal range, as contrasted to its marked elevation prior to treatment Example 4

Intravascular Detection and Therapy of a Thrombosed Myocardial Artery

A male presents with disabling angina pectoris and suspected coronary artery disease. It is decided to examine the coronary arteries and a catheter is inserted by the percutaneous femoral technique. The catheter had a fiberoptic system similar to the ones used in colonoscopy above, but miniaturized with transmission of fluorescence and laser light without the need to visualize the tissues, only to measure fluorescence emitted. A similar DHE preparation as in Example 2(B), conjugated to monoclonal antibody EPB-1 (LL1), which targets atherosclerotic plaques, is injected at a dose of 1.0 mg per kg body weight i.v. Using an excimer-dye laser which emits 405 nm laser beams for diagnosis, the catheter finds an increased signal of fluorescence (translated into an auditory signal whose pitch reflects fluorescence intensity, using a photomultiplier) in the patient's left anterior descending artery. Thereafter, the laser emits a 630 nm laser beam through the optical fiber in the catheter for dissolving the atherosclerotic plaque, keeping the fiber input energy below 4 mJ/pulse. Follow-up reveals that the occluded vessel improved its blood flow by at least 70% without any adverse effects to the patient. The patient's symptoms and cardiac status improves in the ensuing 8 weeks.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method of close-range detection of lesions during an operative, endoscopic, laparoscopic, intravascular catheter, or surgical procedure, wherein the method comprises:
    (a) injecting a patient who is to undergo such a procedure with a bispecific antibody fragment or subfragment with a molecular weight of 85,000 daltons or less, wherein the bispecific antibody fragment has a first antibody binding site which specifically binds to an antigen produced or associated with a lesion, and has a second antibody binding site which specifically binds to a hapten, and permitting the antibody fragment to accrete at target sites;
    (b) injecting a bivalent labeled hapten, which quickly localizes at the target site and clears through the kidneys; and
    (c) detecting the presence of the hapten by close-range detection of elevated levels of accreted label at the target sites with detection means, within 48 hours of the first injection, and conducting said procedure.

2. The method of claim 1, further comprising after step (a), the step of injecting said patient with a clearing composition comprising an agent to clear circulating said bispecific antibody.

3. The method of claim 2, wherein said clearing composition comprises an anti-idiotype antibody.

4. The method of claim 3, wherein said anti-idiotype antibody is conjugated to a galactosyl residue.

5. The method of claim 1, wherein said antigen produced or associated with a lesion is a tumor- or pathogen-associated antigen.

6. The method of claim 1, further comprising the step of removing lesions at sites of elevated label accretion with a laser therapy, brachytherapy, chemo immunotherapy, radio immunotherapy, phototdynamic therapy, external beam irradiation or surgical removal.

7. The method of claim 1, further comprising the step of treating lesions at sites of elevated label accretion with ionizing radiation.

8. The method of claim 1, wherein the procedure is selected from the group consisting of an endoscope, laparoscope, and intravascular catheter procedures, further comprising the step of administering brachytherapy via the endoscope or catheter to lesions at sites of elevated label accretion.

9. The method of claim 1, wherein the lesion is selected from the group consisting of a cancer, an infectious lesion, an inflammatory lesion, a non-tumorous lesion, a clot, hyperplasia and atherosclerotic plaque.

10. The method of claim 1, wherein said procedure is a laparoscopic procedure.

11. The method of claim 1, wherein said hapten is labeled with a diagnostic radioisotope, a MRI image enhancing agent or a fluorescent label.

12. The method of claim 11, wherein said MRI image enhancing agent is a paramagnetic metal.

13. The method of claim 11, wherein said paramagnetic metal is Mn or Gd.

14. The method of claim 11, wherein the label of said diagnostic radioisotope is a gamma, beta or positron emitter.

15. The method of claim 14, wherein diagnostic radioisotope has an energy of 20–1,000 keV.

* * * * *